United States Patent
Jaaskelainen et al.

(10) Patent No.: US 10,337,316 B2
(45) Date of Patent: Jul. 2, 2019

(54) DISTRIBUTED ACOUSTIC SENSING SYSTEM WITH VARIABLE SPATIAL RESOLUTION

(71) Applicant: Halliburton Energy Services, Inc., Houston, TX (US)

(72) Inventors: Mikko Jaaskelainen, Katy, TX (US); Kwang Il Suh, Stevenson Ranch, CA (US); Ira Jeffrey Bush, Los Angeles, CA (US)

(73) Assignee: Halliburton Energy Services, Inc., Houston, TX (US)

( * ) Notice: Subject to any disclaimer, the term of this patent is extended or adjusted under 35 U.S.C. 154(b) by 46 days.

(21) Appl. No.: 15/797,024

(22) Filed: Oct. 30, 2017

(65) Prior Publication Data
US 2018/0058196 A1    Mar. 1, 2018

Related U.S. Application Data

(63) Continuation-in-part of application No. 14/907,790, filed as application No. PCT/US2013/057699 on Aug. 30, 2013, now Pat. No. 9,869,795.

(51) Int. Cl.
*G01V 1/42* (2006.01)
*G01V 1/48* (2006.01)
(Continued)

(52) U.S. Cl.
CPC ............ *E21B 47/101* (2013.01); *E21B 47/14* (2013.01); *G01D 5/35303* (2013.01); *G01V 1/42* (2013.01);
(Continued)

(58) Field of Classification Search
CPC ... G01V 1/48; G01V 8/12; G01V 8/14; G01V 8/16; G01V 8/20; G01D 5/35303;
(Continued)

(56) References Cited

U.S. PATENT DOCUMENTS

| 4,931,771 A | 6/1990 | Kahn |
| 5,194,847 A | 3/1993 | Taylor et al. |

(Continued)

OTHER PUBLICATIONS

International Search Report and Written Opinion issued in related PCT Application No. PCT/US2013/057699 dated May 19, 2014, 9 pages.

(Continued)

*Primary Examiner* — Michael A Lyons
(74) *Attorney, Agent, or Firm* — John W. Wustenberg; Baker Botts L.L.P.

(57) ABSTRACT

Systems and methods for distributed acoustic sensing based on coherent Rayleigh scattering are disclosed herein. A system comprises a pulse generator, an interferometer, a photo detector assembly, and an information handling system. The interferometer comprises a first and second optical switch each comprising a plurality of ports. The information handling system activates one port on each of the first and second optical switches so as to vary the optical path length of the interferometer. A method comprises splitting backscattered light from an optical pulse into a first portion and a second portion, activating one port of a first optical switch and one port of a second optical switch, sending the first portion into a first arm of an interferometer, sending the second portion into a second arm of the interferometer, combining the first and second portions to form an interferometric signal, and receiving the interferometric signal at a photodetector assembly.

17 Claims, 8 Drawing Sheets

(51) Int. Cl.
*G01V 8/10* (2006.01)
*E21B 47/10* (2012.01)
*E21B 47/14* (2006.01)
*G01D 5/353* (2006.01)

(52) U.S. Cl.
CPC ........... *G01D 5/35358* (2013.01); *G01V 1/48* (2013.01); *G01V 8/10* (2013.01)

(58) Field of Classification Search
CPC ..... G01D 5/35338; E21B 47/00; E21B 47/10; E21B 47/123; E21B 47/14
See application file for complete search history.

(56) References Cited

U.S. PATENT DOCUMENTS

| | | | |
|---|---|---|---|
| 6,380,534 B1 | 4/2002 | Farhadiroushan et al. | |
| 6,542,228 B1* | 4/2003 | Hartog | G01M 11/3127 356/73.1 |
| 7,400,408 B2 | 7/2008 | Drabarek et al. | |
| 7,488,930 B2 | 2/2009 | Ajgaonkar et al. | |
| 9,651,709 B2* | 5/2017 | Jaaskelainen | E21B 47/00 |
| 9,869,795 B2* | 1/2018 | Jaaskelainen | E21B 47/00 |
| 2008/0013964 A1* | 1/2008 | Noheji | H04B 10/66 398/202 |
| 2012/0162639 A1 | 6/2012 | Farhadiroushan et al. | |
| 2013/0100768 A1 | 4/2013 | Lopez et al. | |
| 2016/0161631 A1* | 6/2016 | Jaaskelainen | E21B 47/00 356/72 |
| 2016/0170081 A1* | 6/2016 | Jaaskelainen | E21B 47/00 73/152.58 |
| 2016/0195412 A1* | 7/2016 | Barfoot | G01V 8/16 250/227.28 |

OTHER PUBLICATIONS

International Preliminary Report on Patentability issued in related PCT Application No. PCT/US2013/057699 dated Mar. 10, 2016, 6 pages.

* cited by examiner

DISTRIBUTED ACOUSTIC SENSING SYSTEM WITH VARIABLE SPATIAL RESOLUTION

CROSS-REFERENCE TO RELATED APPLICATIONS

This application is a continuation-in-part application of and claims priority to U.S. patent application Ser. No. 14/907,790, entitled "Distributed Acoustic Sensing System with Variable Spatial Resolution" filed Jan. 26, 2016, which claims priority to PCT Application Serial No. PCT/US2013/057699 entitled "Distributed Acoustic Sensing System with Variable Spatial Resolution" filed Aug. 30, 2013, the entire disclosures of which are incorporated by reference herein.

BACKGROUND

This disclosure generally relates to monitoring of hydrocarbon wellbores. In particular, this disclosure relates to systems and methods for monitoring a wellbore using Distributed Acoustic Sensing (DAS).

When performing subterranean operations, acoustic sensing may be used to measure many important properties and conditions of a wellbore, pipeline, other conduit/tube, or fluids used. For example, when performing subterranean operations, it may be desirable to monitor a number of properties related to the subterranean formation and/or conduits used downhole, including, but not limited to, pressure, temperature, porosity, permeability, density, mineral content, electrical conductivity, and bed thickness. Further, certain properties of fluids used in conjunction with performance of subterranean operations, such as pressure, temperature, density, viscosity, chemical elements, and the content of oil, water, and/or gas, may also be important measurements. In addition, downhole-logging tools based on sonic well logging systems may be used to measure downhole properties such as formation porosity, location of bed boundaries and fluid interfaces, well casing condition, and behind casing cement location and bonding quality. Monitoring properties and conditions over time may have significant value during exploration and production activities.

A DAS system may be capable of producing the functional equivalent of 10 s, 100 s, or even 1000 s of acoustic sensors. Properties of downhole formations surrounding or otherwise adjacent to a wellbore may be monitored over time based on the acoustic sensing. Further, hydrocarbon production may be controlled, or reservoirs may be managed based on the downhole formation properties sensed by in-well acoustic measurement methods using a DAS system.

Acoustic sensing based on DAS may use the Rayleigh backscatter property of a fiber's optical core and may spatially detect disturbances that are distributed along the fiber length. Such systems may rely on detecting phase changes brought about by changes in strain along the fiber's core. Externally-generated acoustic disturbances may create very small strain changes to optical fibers. The acoustic disturbance may also be reduced or masked by a cable in which the fiber is deployed.

BRIEF DESCRIPTION OF THE DRAWINGS

These drawings illustrate certain aspects of certain embodiments of the present disclosure. They should not be used to limit or define the disclosure.

Figure 1:
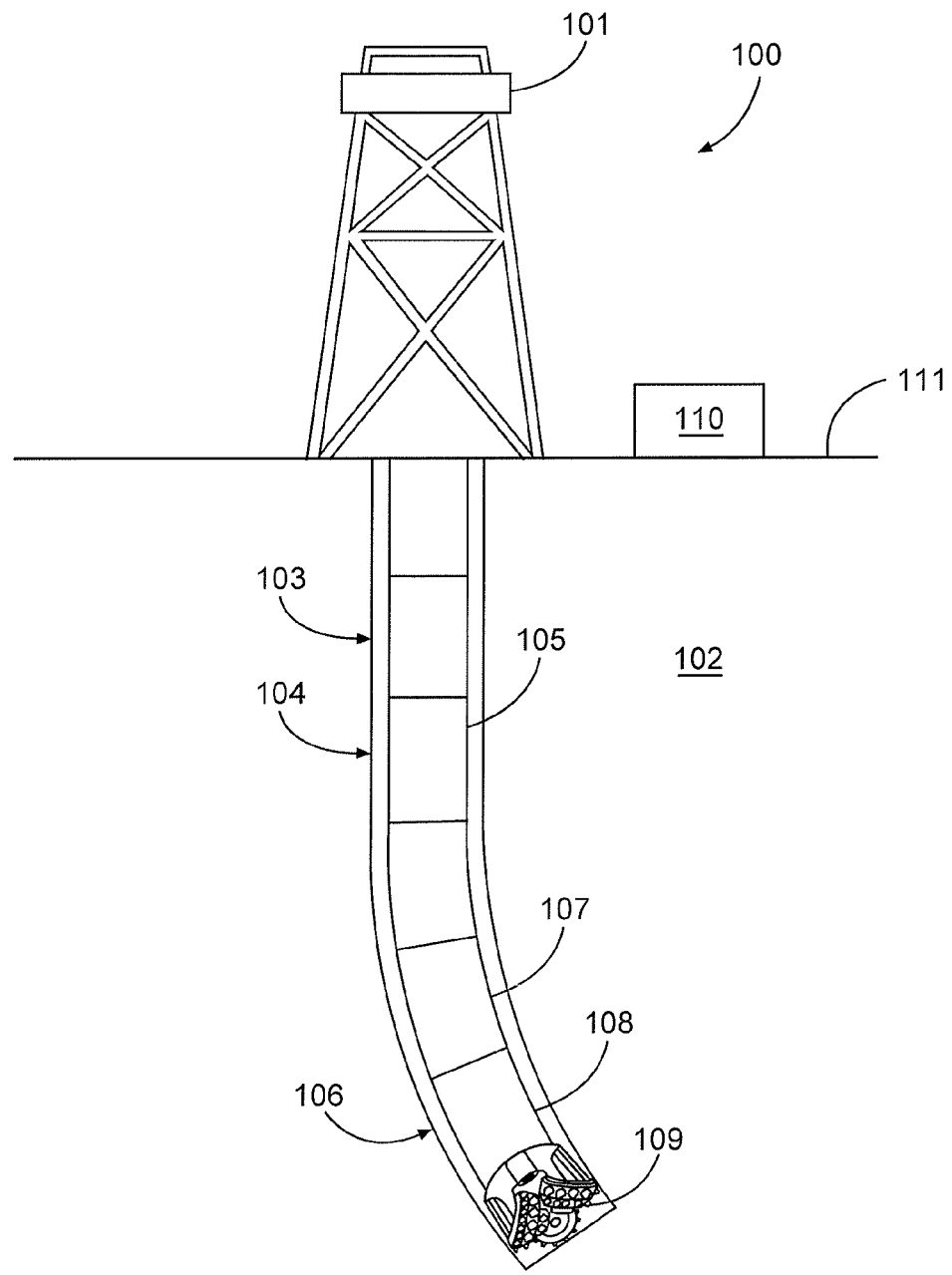
FIG. 1 depicts a hydrocarbon drilling site in accordance with one embodiment of the present disclosure.

While embodiments of this disclosure have been depicted and described and are defined by reference to example embodiments of the disclosure, such references do not imply a limitation on the disclosure, and no such limitation is to be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

DETAILED DESCRIPTION

Illustrative embodiments of the present disclosure are described in detail herein. In the interest of clarity, not all features of an actual implementation may be described in this specification. It will of course be appreciated that in the development of any such actual embodiment, numerous implementation-specific decisions may be made to achieve the specific implementation goals, which may vary from one implementation to another. Moreover, it will be appreciated that such a development effort might be complex and time-consuming, but would nevertheless be a routine undertaking for those of ordinary skill in the art having the benefit of the present disclosure.

The terms "couple" or "couples" as used herein are intended to mean either an indirect or a direct connection. Thus, if a first device couples to a second device, that connection may be through a direct connection, or through an indirect electrical or mechanical connection via other devices and connections. The term "upstream" as used herein means along a flow path towards the source of the flow, and the term "downstream" as used herein means along a flow path away from the source of the flow. The term "uphole" as used herein means along the drillstring or the hole from the distal end towards the surface, and "downhole" as used herein means along the drillstring or the hole from the surface towards the distal end.

It will be understood that the term "oil well drilling equipment" or "oil well drilling system" is not intended to limit the use of the equipment and processes described with those terms to drilling an oil well. The terms also encompass drilling natural gas wells or hydrocarbon wells in general. Further, such wells can be used for production, monitoring, or injection in relation to the recovery of hydrocarbons or other materials from the subsurface. This could also include geothermal wells intended to provide a source of heat energy instead of hydrocarbons.

For purposes of this disclosure, an information handling system may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, an information handling system may be a personal computer, a network storage device, or any other suitable device and may vary in size, shape, performance, functionality, and price. The information handling system may include random access memory ("RAM"), one or more processing resources such as a central processing unit ("CPU") or hardware or software control logic, ROM, and/or other types of nonvolatile memory. Additional components of the information handling system may include one or more disk drives, one or more network ports for communication with external devices as well as various input and output ("I/O") devices, such as a keyboard, a mouse, and a video display. The information handling system may also include one or more buses operable to transmit communications between the various hardware components.

For the purposes of this disclosure, computer-readable media may include any instrumentality or aggregation of instrumentalities that may retain data and/or instructions for a period of time. Computer-readable media may include, for example, without limitation, storage media such as a direct access storage device (e.g., a hard disk drive or floppy disk drive), a sequential access storage device (e.g., a tape disk drive), compact disk, CD-ROM, DVD, RAM, ROM, electrically erasable programmable read-only memory ("EEPROM"), and/or flash memory; as well as communications media such as wires.

To facilitate a better understanding of the present disclosure, the following examples of certain embodiments are given. In no way should the following examples be read to limit, or define, the scope of the disclosure. Embodiments of the present disclosure may be applicable to horizontal, vertical, deviated, multilateral, u-tube connection, intersection, bypass (drill around a mid-depth stuck fish and back into the wellbore below), or otherwise nonlinear wellbores in any type of subterranean formation. Certain embodiments may be applicable, for example, to logging data acquired with wireline, slickline, and logging-while-drilling/measurement-while-drilling (LWD/MWD) methods. Certain embodiments may be applicable to subsea and/or deep sea wellbores. Embodiments described below with respect to one implementation are not intended to be limiting.

FIG. 1 illustrates an example drilling system 100 according to aspects of the present disclosure. The drilling system 100 includes a rig 101 located at a surface 111 and positioned above a wellbore 103 within a subterranean formation 102. In certain embodiments, a drilling assembly 104 may be coupled to the rig 101 using a drill string 105. In other embodiments, the drilling assembly 104 may be coupled to the rig 101 using a wireline or a slickline, for example. The drilling assembly 104 may include a bottom hole assembly (BHA) 106. The BHA 106 may include a drill bit 109, a steering assembly 108, and a LWD/MWD apparatus 107. A control unit 110 located at the surface 111 may include a processor and memory device, and may communicate with elements of the BHA 106, in the LWD/MWD apparatus 107 and the steering assembly 108. In certain implementations, the control unit 110 may be an information handling system.

The control unit 110 may receive data from and send control signals to the BHA 106. Additionally, at least one processor and memory device may be located downhole within the BHA 106 for the same purposes. The LWD/MWD apparatus 107 may log the formation 102 both while the wellbore 103 is being drilled, and after the wellbore is drilled to provide information regarding ongoing subterranean operations. The steering assembly 108 may include a mud motor that provides power to the drill bit 109, and that is rotated along with the drill bit 109 during drilling operations. The mud motor may be a positive displacement drilling motor that uses the hydraulic power of the drilling fluid to drive the drill bit 109. In accordance with an exemplary embodiment of the present disclosure, the BHA 106 may include an optionally non-rotatable portion. The optionally non-rotatable portion of the BHA 106 may include any of the components of the BHA 106, excluding the mud motor and the drill bit 109. For instance, the optionally non-rotatable portion may include a drill collar, the LWD/MWD apparatus 107, bit sub, stabilizers, jarring devices and crossovers. In certain embodiments, the steering assembly 108 may angle the drill bit 109 to drill at an angle from the wellbore 103. Maintaining the axial position of the drill bit 109 relative to the wellbore 103 may require knowledge of the rotational position of the drill bit 109 relative to the wellbore 103.

Figure 2:
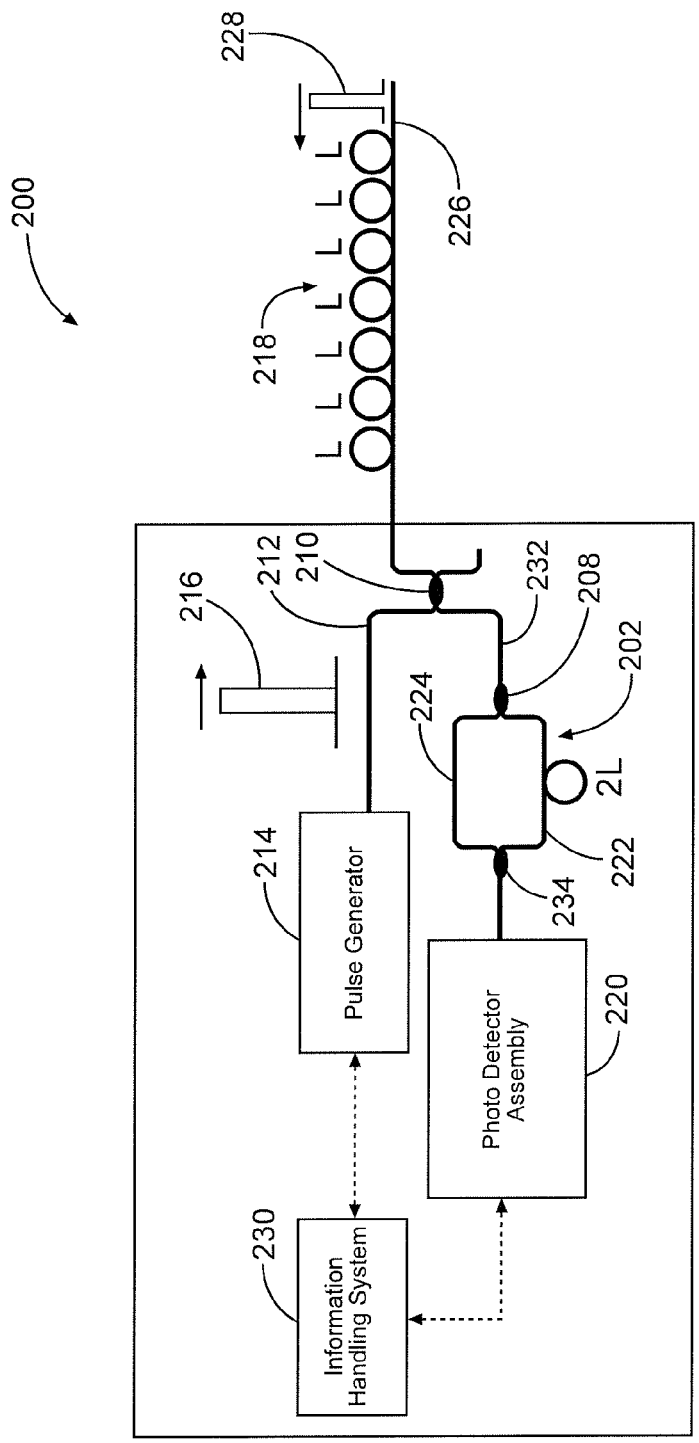
FIG. 2 depicts a distributed acoustic sensing system.

Referring now to FIG. 2, a system for performing Distributed Acoustic Sensing (DAS) is referenced generally by reference numeral 200. The system 200 may be incorporated into the drilling assembly 104 and lowered downhole using a drill string, by wireline, slickline, coiled tubing, or by any other means known to those in the art having the benefit of this disclosure. Alternatively, the system 200 or a portion of the system 200 may be positioned downhole for permanent monitoring and coupled to the casing or tubing. The system 200 may be a single pulse coherent Rayleigh scattering system with a compensating inferometer but is not intended to be limited to such.

Still referring to FIG. 2, a pulse generator 214 may be coupled to a first coupler 210 using the optical fiber 212. The pulse generator 214 may be located at any suitable location when performing subterranean operations. For instance, in some embodiments, the pulse generator 214 may be located at the surface of the wellbore 103. The pulse generator 214 may include associated opto-electronics and laser. The first coupler 210 may be a traditional fused-type fiber optic splitter, a circulator, a PLC fiber optic splitter, or any other type of splitter known to those with ordinary skill in the art having the benefit of this disclosure. In other embodiments, the first coupler 210 may be a circulator. Optical pulses from the pulse generator 214 may be amplified using optical gain elements, such as any suitable amplification mechanisms including, but not limited to, Erbium Doped Fiber Amplifiers (EDFAs) or Semiconductor Optical Amplifiers (SOAs).

Still referring to FIG. 2, a second coupler 208 may be coupled to an interferometer 202. The second coupler 208 may split light from the optical fiber 232 into two paths along a top interferometer arm 224 and a bottom interferometer arm 222. In other words, the second coupler 208 may split the backscattered light (e.g., backscattered light 228) from the optical fiber 232 into a first backscattered pulse and a second backscattered pulse. The first backscattered pulse may be sent into the top interferometer arm 222. The second backscattered pulse may be sent into the bottom interferometer arm 224. The first and second backscattered pulses from the top and bottom interferometer arms 222, 224 are then re-combined at a third coupler 234 to form an interferometric signal. The first, second, and third couplers 210, 208, and 232 may be a traditional fused type fiber optic splitter, a PLC fiber optic splitter, or any other type of splitter known to those with ordinary skill in the art having the benefit of this disclosure.

The interferometer 202 may be used to determine the relative phase shift variations between the light in the top interferometer arm 224 and the bottom interferometer arm 222 as they recombine. The interferometric signal, i.e., the relative phase shift, will vary over the distance of the distributed optical fiber 226, and the location of the interferometric signal can be determined using time of flight for the optical pulse 216. In the illustrative embodiment of FIG. 2, the interferometer is a Mach-Zehnder interferometer, but it is not intended to be limited to such. For instance, in certain implementations, a Michelson interferometer or any other type of interferometer known to those of skill in the art having the benefit of this disclosure may also be used without departing from the scope of the present disclosure.

The interferometer 202 may be coupled to a photodetector assembly 220. The photodetector assembly 220 may include associated optics and signal processing electronics (not shown). The photodetector assembly 220 may be a semiconductor electronic device that uses the photoelectric effect to convert light to electricity. The photodetector assembly 220 may be an avalanche photodiode or a pin photodiode but is not intended to be limited to such. As the light from the top interferometer arm 224 and the bottom interferometer arm 222 reach the third coupler 234, the photodetector assembly 220 may convert the optical signal (i.e., the interferometric signal) to an electronic signal proportional to the acoustic signal along the distributed optical fiber 226. The photodetector assembly 220 may be coupled to an information handling system 230. The photodetector assembly 220 and information handling system 230 may be communicatively and/or mechanically coupled. A first device may be communicatively coupled to a second device if it is connected to the second device through a wired or wireless communication network which permits the transmission of information. Thus, the information handling system 230 may be located uphole, downhole, or at a remote location. The information handling system 230 may also be communicatively or mechanically coupled to the pulse generator 214.

In operation of the system 200, the pulse generator 214 may generate a first optical pulse 216 which is transmitted through the optical fiber 212 to the first coupler 210. In certain implementations, the pulse generator 214 may be a laser. The first coupler 210 may direct the first optical pulse 216 through the optical fiber 226. At least a portion of the optical fiber 226 may be arranged in coils 218. As the first optical pulse 216 travels through the optical fiber 226, imperfections in the optical fiber 226 may cause a portion of the light to be backscattered along the optical fiber 226 due to Rayleigh scattering. Scattered light according to Rayleigh scattering is returned from every point along the optical fiber 226 along the length of the optical fiber 226 and is shown as backscattered light 228 in FIG. 2. This backscatter effect may be referred to as Rayleigh backscatter. Density fluctuations in the optical fiber 226 may give rise to energy loss due to the scattered light, with the following coefficient:

$$\alpha_{scat} = \frac{8\pi^3}{3\lambda^4} n^8 p^2 k T_f \beta$$

where n is the refraction index, p is the photoelastic coefficient of the optical fiber 226, k is the Boltzmann constant, and β is the isothermal compressibility. $T_f$ is a fictive temperature, representing the temperature at which the density fluctuations are "frozen" in the material. The optical fiber 226 may be terminated with a low reflection device (not shown). In certain implementations, the low reflection device (not shown) may be a fiber coiled and tightly bent to violate Snell's law of total internal reflection such that all the remaining energy is sent out of the fiber. In other implementations, the low reflection device (not shown) may be an angle cleaved fiber. In still other implementations, the low reflection device (not shown) may be a coreless optical fiber with high optical attenuation. In still other implementations, the low reflection device (not shown) may be a termination, such as the AFL Endlight.

The backscattered light 228 may travel back through the optical fiber 226, until it reaches the second coupler 208. The first coupler 210 may be mechanically coupled to the second coupler 208 on one side by the optical fiber 232 such that the backscattered light 228 may pass from the first coupler 210 to the second coupler 208 through the optical fiber 232. The second coupler 208 may split the backscattered light 228 based on the number of interferometer arms so that one portion of any backscattered light 228 passing through the interferometer 202 travels through the top interferometer arm 224 and another portion travels through the bottom interferometer arm 222. In other words, the second coupler 208 may split the backscattered light from the optical fiber 232 into a first backscattered pulse and a second backscattered pulse. The first backscattered pulse may be sent into the top interferometer arm 222. The second backscattered pulse may be sent into the bottom interferometer arm 224. These two portions may be re-combined at the third coupler 234, and at that point, they may generate an interferometric signal. In an interferometric signal, two signals are superimposed from points separated by a distance of L, where L is the difference in length between the top interferometer arm 224 and bottom interferometer arm 222. The output from the compensating interferometer 202, or the interferometric signal, includes backscattered interfered light from two positions. This interferometric signal may reach the photodetector assembly 220, where it may be converted to an electrical signal. The photodetector assembly 220 may integrate or add up the number of photons received in a given time period. The photodetector assembly 220 may provide output relating to the backscattered light 228 to the information handling system 230, which may convey the data to a display and/or store it in computer-readable media.

Figure 3:
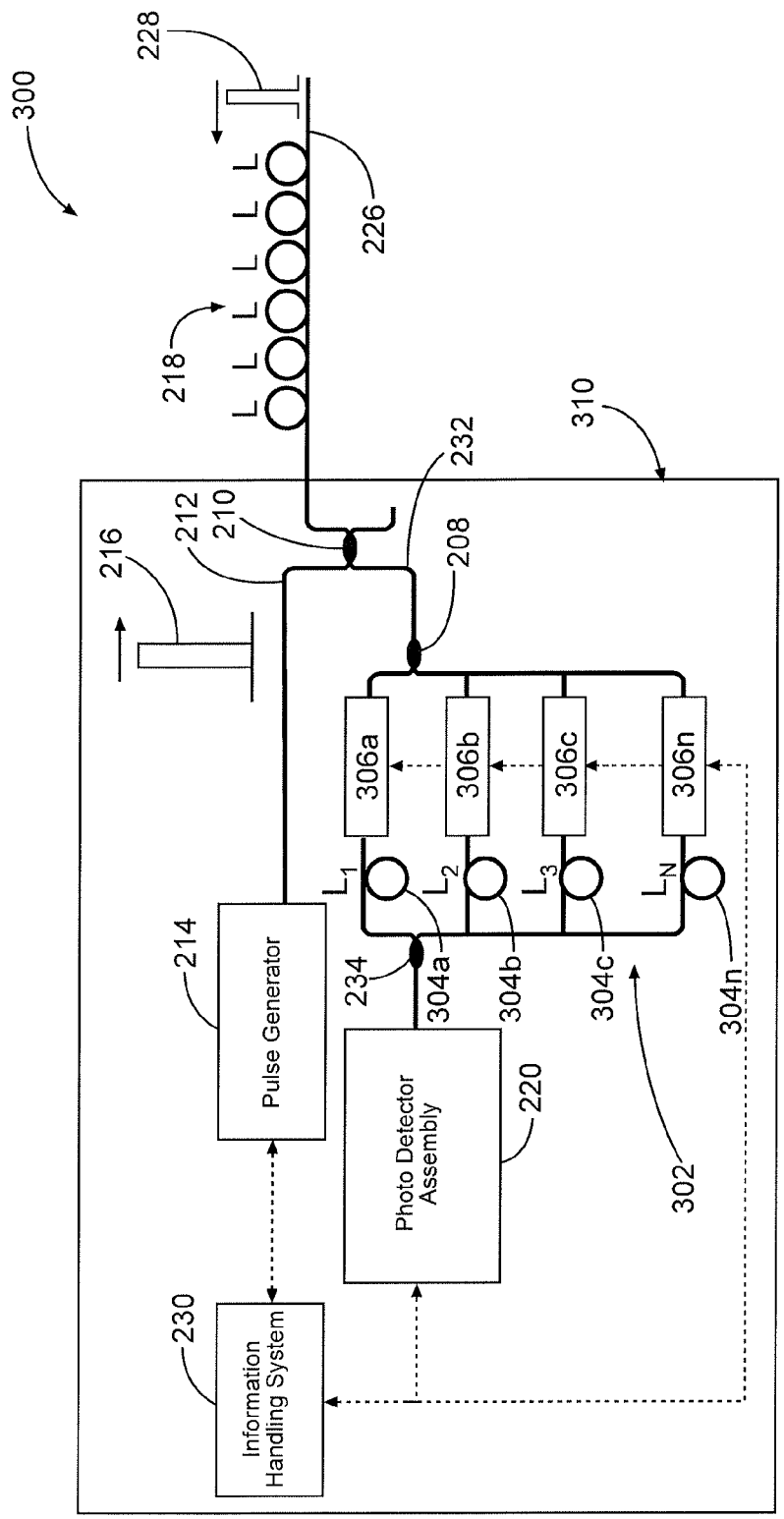
FIG. 3 depicts a distributed acoustic sensing system in accordance with one embodiment of the present disclosure.

Referring now to FIG. 3, an exemplary system for performing Distributed Acoustic Sensing (DAS) is referenced generally by reference numeral 300. A DAS interrogation unit 310 includes the information handling system 230, the pulse generator 214 coupled to the information handling system 230, the photodetector assembly 220 coupled to the information handling system 230, and an interferometer 302 coupled to the photodetector assembly 220. As shown in FIG. 3, the optical fiber 226 may be disposed between the interferometer 302 and the pulse generator 214 but other configurations are possible. The optical fiber 226 may be lowered downhole, but the DAS interrogation unit 310 may be located at the surface. Specifically, the optical fiber 226 may be coupled to a casing or tubing.

Still referring to FIG. 3, the system 300 may include the interferometer 302. The interferometer 302 may include three or more interferometer arms 304a-N that may be selectively engaged. Each interferometer arm 304a-N may be coupled to an optical gain element 306a-N, and each optical gain element 306a-N may be coupled to the information handling system 230. The interferometer arms 304a-N may each be of a different length. The interferometer arms 304a-N may be arranged in coils. However, the disclosure is not intended to be limited to any number or combination of coils. An optical gain element 306a-N may include any amplifier of optical transmissions that uses any suitable means to achieve desired gains and/or any desired attenuation element that may prohibit light from passing through the selected interferometer arms. An example of an attenuation element is a Variable Optical Attenuator (VOA). For instance, in certain implementations, a semiconductor optical amplifier or rare earth doped fiber or any other optical amplification medium known to those with skill in the art may be used to achieve gains. In some embodiments, the optical amplification medium may be replaced with VOAs that may be used to attenuate selected interferometer arms while allowing light to pass through other interferometer arms with minimum attenuation.

Still referring to FIG. 3, the interferometer 302 may be communicatively and/or mechanically coupled to a photodetector assembly 220. The photodetector assembly 220 may include associated optics and signal processing electronics. The photodetector assembly 220 may be coupled to an information handling system 230. The information handling system 230 may be located downhole, uphole, or at a remote location. A second coupler 208 may be part of the interferometer 302. A first coupler 210 may be coupled at one side to the second coupler 208 and at the other side, to an optical fiber 212. A pulse generator 214 may be coupled to the first coupler 210 using the optical fiber 212. The pulse generator 214 may include associated opto-electronics and a laser but is not intended to be limited to such. The pulse generator 214 may be located at any suitable location when performing subterranean operations. For instance, in some embodiments, the pulse generator 214 may be located at the surface of the wellbore 103.

In operation of the system 300, the pulse generator 214 may generate a first optical pulse 216 which is transmitted through the optical fiber 212 to the first coupler 210. The optical pulse may be optically amplified using optical gain elements, for example, Erbium Doped Fiber Amplifiers (EDFAs) or Semiconductor Optical Amplifiers (SOAs). The first coupler 210 may direct the first optical pulse 216 through the optical fiber 226. At least a portion of the optical fiber 226 may be arranged in coils 218. As the pulse 216 travels through the optical fiber 226, imperfections in the optical fiber 226 may cause light to be reflected back along the optical fiber 226. Backscattered light 228 according to Rayleigh scattering may be returned from every point along the optical fiber 226 along the length of the optical fiber 226. This backscatter effect may be referred to as Rayleigh backscatter. The optical fiber 226 may be terminated with a low reflection device (not shown). In certain implementations, the low reflection device (not shown) may be a fiber coiled and tightly bent to violate Snell's law of total internal reflection such that all the remaining energy is sent out of the fiber. In other implementations, the low reflection device (not shown) may be an angle cleaved fiber. In still other implementations, the low reflection device (not shown) may be a coreless optical fiber with high optical attenuation. In still other implementations, the low reflection device (not shown) may be a termination, such as the AFL Endlight.

Still referring to FIG. 3, the backscattered light 228 may travel back through the optical fiber 226 until it reaches the second coupler 208. The second coupler 208 may be coupled to an interferometer 302. The second coupler 208 may split the backscattered light 228 from the optical fiber 232 into various paths along the interferometer arms 304a-N. Two of the optical gain elements 306a-N may be active and turned on to allow light to pass through, and they may provide gain on two selected interferometer arms (for example, 304a and 304b) while all the other optical gain elements may be turned off to provide high attenuation. Thus, there may be high optical attenuation in the remaining interferometer arms (for example, 304c-N). The two active optical paths will form an interferometer, and the difference in path length will be dependent on which optical gain elements 306a-N are active and which optical gain elements 306a-N are turned off. Thus, the second coupler 208 may split the backscattered light from the optical fiber 232 into a number of backscattered pulses, based on the number of interferometer arms in the interferometer 302. A first backscattered pulse may be sent into a top interferometer arm. A second backscattered pulse may be sent into a bottom interferometer arm. The interferometer arms 304a-N may then be re-combined at a third coupler 234, and the first and second backscattered pulses from the selected active interferometer arms may be re-combined to form an interferometric signal. The interferometric signal is comprised of backscattered interfered light. In an interferometric signal, two signals are superimposed from points separated by a distance of L, where L is the difference in length between the top interferometer arm and bottom interferometer arm. The interferometric signal (i.e., the backscattered interfered light) may be representative of a downhole condition. For example, the downhole condition may include, but is not limited to: perforating, operating downhole hardware, monitoring downhole pumps, sensing acoustic signals during fracturing and in-flow stimulation, water injection, production monitoring, flow regimes, reflection seismic, microseismic, and acoustic events related to well-bore integrity (e.g., leaks, cross-flow, and formation compaction). The interferometric signal may also be representative of a condition on pipelines, flow-lines and risers related to flow, leaks, integrity, pigging and maintenance. Further, the interferometric signal may also be representative of conditions on subsea equipment where rotating equipment may cause vibration and/or acoustic noise. Similarly, the interferometric signal may be representative of a condition on infrastructure and security monitoring where it may be beneficial to dynamically vary the optical path length in the system 300.

Still referring to FIG. 3, the photodetector assembly 220 may convert the interferometric signal (i.e., an optical signal) to an electrical signal proportional to the acoustic signal along the distributed optical fiber 226. The photodetector assembly 220 may be an avalanche photodiode or a pin photodiode but is not intended to be limited to such. The photodetector assembly 220 may include associated optics and signal processing electronics that may be used to measure the voltage of the light incoming from the interferometer 202. The photodetector assembly 220 may be coupled to an information handling system 230. The photodetector assembly 220 and information handling system 230 may be communicatively and/or mechanically coupled. Thus, the information handling system 230 may be located uphole, downhole, or at a remote location. The information handling system 230 may also be communicatively and/or mechanically coupled to the pulse generator 214. The photodetector assembly 220 may integrate or add up the number of photons received in a given time period. The photodetector assembly 220 may provide output relating to the back reflected light to the information handling system 230, which may convey the data to a display and/or store it in computer-readable media.

The optical pulse 216 may travel down the length of the optical fiber 226 while generating backscattered light 228 from various positions along the length of the optical fiber 226. The time at which the optical pulse 216 is sent from the pulse generator 214, and the time it takes for the backscattered light 228 to travel to the photodetector assembly 220 may be measured accurately. The velocity of the optical pulse 216 as it travels down the optical fiber 226 may be well known. The location of any backscattered light 228 may then simply be calculated by measuring the time at which it reaches the photodetector assembly 220, i.e., a time-of-flight measurement. Using contiguous readings over the time it takes for the backscattered light 228 to traverse the optical fiber 218, a measurement may be collected at the photodetector assembly 220 relating to how the back reflected light varies over the length of the optical fiber 226.

The interferometer arms 304a-N may each be of a different length. Thus, various combinations of optical gain element 306a-N may be selectively activated such that the backscattered light 228 may travel through them and the interferometer arm 304a-N coupled to them, thereby varying the distance over which the reflected optical pulse 228 may travel. Each optical gain element 306a-N may be communicatively coupled to a control unit (not shown) such that a user may select which optical gain elements 306a-N may be engaged at any given time. In certain implementations, the control unit may be an information handling system. Alternatively, the optical gain elements 306a-N may be engaged according to an automated program. Thus, the sensitivity and spatial resolution of the system 300 may be changed in-situ depending on the needs of the system 300. Applications where active sources are used may generate strong acoustic signals, and users may prefer to have the system settings selected to provide higher spatial resolution with good signal-to-noise ratios. The well depth as well as the associated signal paths may vary. Thus, shallow applications may have a stronger signal, whereas signals in deep wells may experience higher signal attenuation due to the longer travel path for acoustic signals. It may therefore be beneficial to change the difference in path length to optimize the signal-to-noise ratio dependent on the attenuation of the acoustic signals or on the application. Other applications may include micro-seismic sensing and/or passive sensing where small micro-seismic events in the formation may generate noise, and it may be beneficial to record these events and use them for reservoir characterization and optimization.

The term "spatial resolution" as used herein refers to the ability to discriminate between two adjacent acoustic events along an optical fiber. It is generally desirable to have a fine spatial resolution in a system to allow for detection of events that are spatially near each other, like perforations in a hydrocarbon well, for example. The spatial resolution of the system 300 is a function of the width of the first optical pulse 216 and the difference in length between the top interferometer arm, which may be any of 304a-304(N−1) and the bottom interferometer arm, which may be any of 304b-304N, depending on which of the arms in the system have activated optical gain elements 306a-N. The sensitivity of the system 300 is a function of the difference in length between the top interferometer arm and the bottom interferometer arm, and a greater difference in length between these two fibers improves the system's sensitivity to acoustic and/or vibrational energy. In other words, greater sensitivity allows the system 300 to detect acoustic and/or vibrational events with smaller signal amplitude.

Additional optical pulses may be sent into the optical fiber 226 from the pulse generator 214 in close succession and at a fixed rate. By measuring the backscattered interfered light from each of these optical pulses at the photodetector assembly 220, a discrete representation of the change in acoustic energy in the wellbore may be measured as a function of time. The changes in acoustic energy may then be correlated with sub-surface events. For example, a change in acoustic energy may be related to a change in flow, a change in solids in a fluid, or a change in the oil/water/gas ratio present in the wellbore 103. The pulse generator 214 may be operable to vary the pulse width of optical pulses it generates. Further, the differential path length difference between two selected interferometer arms may be varied. In this way, the spatial resolution of the system 300 may be varied.

Figure 4:
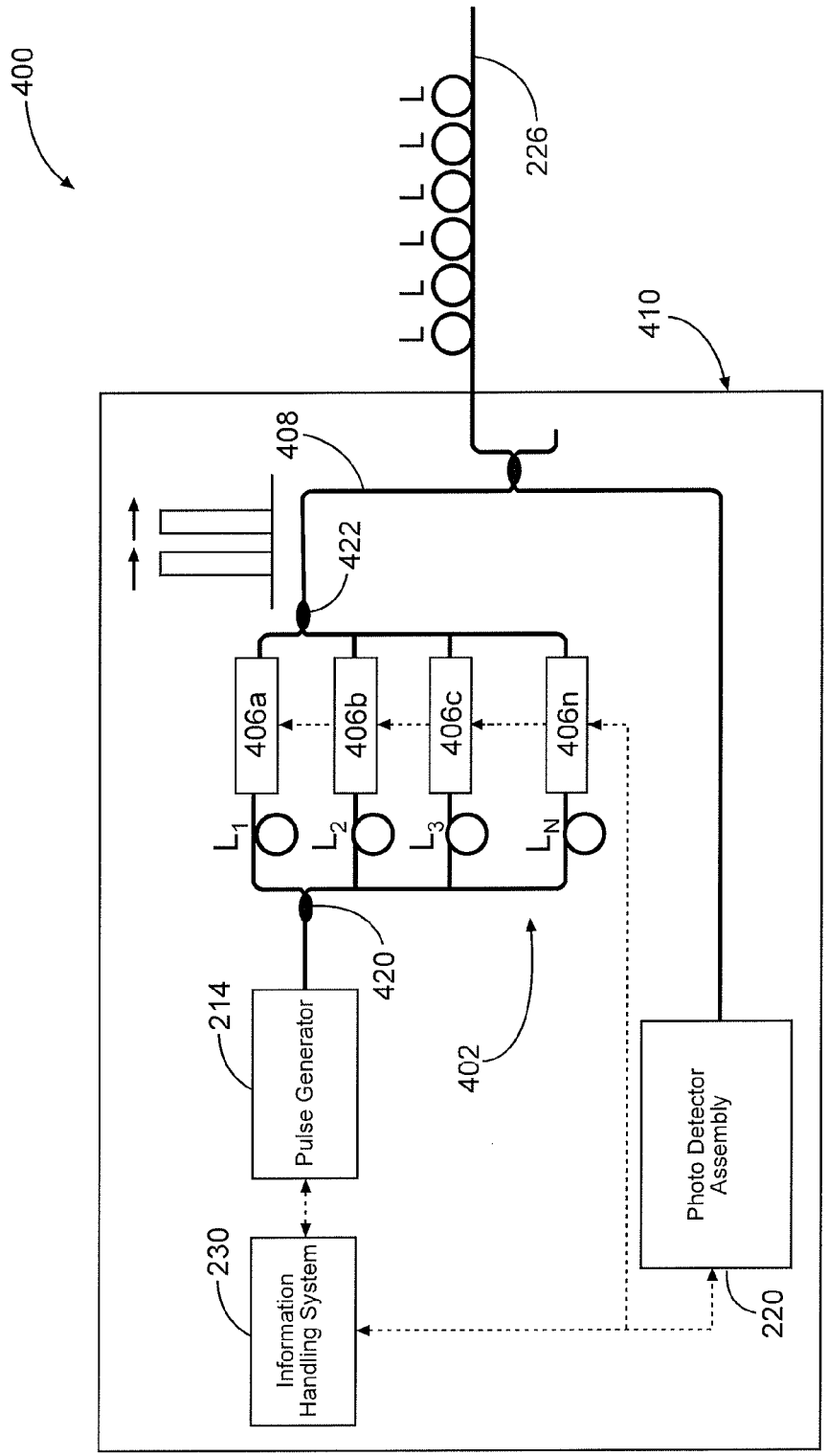
FIG. 4 depicts a distributed acoustic sensing system in accordance with an alternative embodiment of the present disclosure.

Referring now to FIG. 4, an exemplary system for performing Distributed Acoustic Sensing (DAS) according to an alternative embodiment of the present disclosure is referenced generally by reference numeral 400. As shown in FIG. 4, the interferometer 402 may be disposed between the pulse generator 214 and the optical fiber 226, although other configurations are possible. The pulse generator 214 may generate a single pulse that may be split in the first coupler 420 into N paths according to the number of active arms in the interferometer 402 (i.e., those arms of interferometer 402 that allow light transmission). For example, two of the N paths may be active. In this example, a first optical pulse may be split into a number of portions, according to the number of arms in the interferometer 402. A first portion of the first optical pulse may be sent into a first active arm of the interferometer 402. A second portion of the first optical pulse may be sent into a second active arm of the interferometer 402. The first portion and the second portion may then both reenter the optical fiber 408 at the second coupler 422. The two portions may be separated in time by a delay proportional to the difference in path length between the selected interferometer arms. Both portions may generate backscattered light as they travel down the optical fiber 226. The backscattered light from the first portion may then interfere with the backscattered light from the second portion. The two portions of backscattered light may interfere in the optical fiber 226, and they may travel in the optical fiber 226 to the photodetector assembly 220, where the backscattered interfered light may be converted to an electrical signal. As discussed with respect to FIG. 3, the backscattered interfered light may be representative of a downhole condition. The downhole condition may include, for example, perforating, operating downhole hardware, monitoring downhole pumps, sensing acoustic signals during fracturing and in-flow stimulation, water injection, production monitoring, flow regimes, reflection seismic, micro-seismic, and acoustic events related to well-bore integrity (e.g., leaks, cross-flow, and formation compaction). The interferometric signal may also be representative of a condition on pipelines, flow-lines and risers related to flow, leaks, integrity, pigging and maintenance. The interferometric signal may also be representative of conditions on subsea equipment where rotating equipment cause vibration and/or acoustic noise. Similarly, the interferometric system signal may be representative of a condition on infrastructure and security monitoring where it may be beneficial to dynamically vary the optical path length in the system 400. The spatial resolution and sensitivity of the system 400 may be tuned by changing which optical gain elements 406a-N are active. As discussed with respect to FIG. 3, the pulse generator 214 may be operable to vary the optical pulse width. Further, the differential path length difference between two selected interferometer arms may be varied. In this way, the spatial resolution of the system 400 may be varied.

In other embodiments, pairs of optical switches may be used to select a desired optical path. The optical switches may be MEMS switches or any other suitable optical switches.

Figure 5:
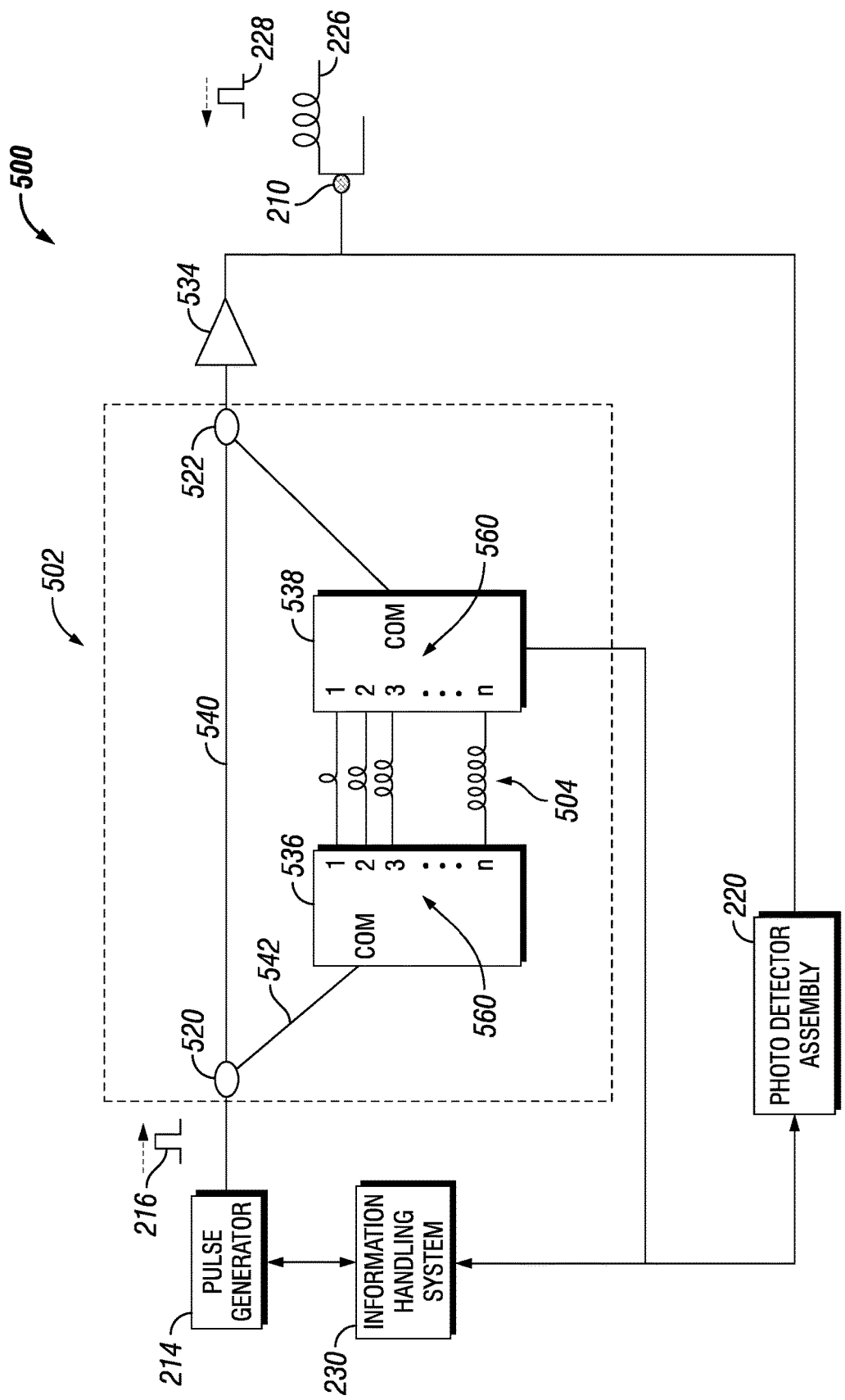
FIG. 5 depicts a distributed acoustic sensing system in accordance with an alternative embodiment of the present disclosure.

Referring now to FIG. 5, an exemplary system for performing Distributed Acoustic Sensing (DAS) according to an alternative embodiment of the present disclosure is referenced generally by reference numeral 500. As shown in FIG. 5, an interferometer 502 may be disposed between a pulse generator 214 and an optical gain device 534, although other configurations are possible. The optical gain device 534 may be any suitable amplifier such as an EDFA. The interferometer 502 may optionally be a pulse delay diplexer. As shown in FIG. 5, the interferometer 502 may include a first coupler 520, a first arm 540, a second arm 542, a first optical switch 536, a second optical switch 538, a plurality of fiber coils 504, and a second coupler 522. The fiber coils 504 may each have a different length. The second arm 542 of the interferometer 502 may be coupled to the first optical switch 536. The first optical switch 536 may be coupled to the second optical switch 538 via the plurality of fiber coils 504. Each optical switch 536 and 538 includes a number of ports 560 that may be selectively engaged to direct light through the associated fiber coils 504.

In operation of the system 500, the pulse generator 214 may generate a single pulse that may be split in the first coupler 520 between the first arm 540 and the second arm 542 of the interferometer 502. The light that is transmitted via the first arm 540 will travel with no delays from the first coupler 520 to the second coupler 522. The light that is sent to the optical fiber 542 will travel with a controlled delay through the first optical switch 536, fiber coils 504, and second optical switch 538. The light will travel into a selected path according to an active fiber coil 504 (i.e., the fiber coil of the fiber coils 504 that allows light transmission, based on an active port 560 of the first switch 536). The state (active or not active) of the ports 560 may be controlled by an information handling system 230. The first optical switch 536 and the second optical switch 538 are preferably 1×n switches such that only one port of each optical switch may be active at any given time. For example, light may travel from port 1 of the first switch 536 to port 1 of the second switch 538. Alternatively, light may travel from port n of the first switch 536 to port n of the second switch 538. The portion of the light that traveled through the first arm 540 is then recombined with the light that traveled through the optical switches at a second coupler 522. The two portions may be separated in time by a delay proportional to the difference in path length of the second arm 542 (including traveling through the second arm 542, the first optical switch 536, the selected fiber coil 504, the second optical switch 538, and to the second coupler 522) and the path length of the first arm 540. Use of the optical switches 536 and 538 eliminates the need to use any optical gain elements within the interferometer 502 because the first and second optical switches 536 and 538 may be used to select a particular singular path delay. This is implicitly efficient as all of the light that travels through the second arm 542 passes through that same delay.

Still referring to FIG. 5, each portion of the optical pulse may be amplified using an optical gain device 534. Both portions may generate backscattered light as they travel down the optical fiber 226. The backscattered light from the first portion may then interfere with the backscattered light from the second portion. The two portions of backscattered light may interfere in the optical fiber 226, and they may travel in the optical fiber 226 to the photodetector assembly 220, where the backscattered interfered light may be converted to an electrical signal.

Still referring to FIG. 5, the use of the optical switches 536 and 538 allows for optical efficiencies because the optical switches 536 and 538 may be used to selectively turn on only one port 560 in each of the optical switches. Thus, the light may travel through only one fiber coil 504. As compared to other embodiments, such as those described in connection with FIGS. 3 and 4, the embodiment shown in FIG. 5 is more optically efficient and therefore preserves optimum sensitivity of the system 500. For example, it is not necessary to use an optical gain device on each fiber coil 504 or anywhere within the interferometer 502. Excess optical gain devices may add noise to the optical signal. Instead, the first optical switch 536 may control which singular fiber coil 504 receives light, and therefore controls the length of the path delay. This is an efficient arrangement because all of the light that travels through the second arm 542 passes through the same fiber coil 504 and therefore the same path delay. The optical switches 536 and 538 are passive during operation of the system 500 and do not add any excess noise during operation.

Still referring to FIG. 5, as discussed with respect to FIG. 3, the backscattered interfered light may be representative of a downhole condition. The downhole condition may include, for example, perforating, operating downhole hardware, monitoring downhole pumps, sensing acoustic signals during fracturing and in-flow stimulation, water injection, production monitoring, flow regimes, reflection seismic, microseismic, and acoustic events related to well-bore integrity (e.g., leaks, cross-flow, and formation compaction). The interferometric signal may also be representative of a condition on pipelines, flow-lines and risers related to flow, leaks, integrity, pigging and maintenance. The interferometric signal may also be representative of conditions on subsea equipment where rotating equipment cause vibration and/or acoustic noise. Similarly, the interferometric system signal may be representative of a condition on infrastructure and security monitoring where it may be beneficial to dynamically vary the optical path length in the system 500. The spatial resolution and sensitivity of the system 500 may be tuned by changing which port 560 of the first optical switch is active. As discussed with respect to FIG. 3, the pulse generator 214 may be operable to vary the optical pulse width. Further, the differential path length difference between the first arm 540 and the fiber coils 504 may be varied by changing which port 560 of the first optical switch is active. In this way, the spatial resolution of the system 500 may be varied.

Figure 6:
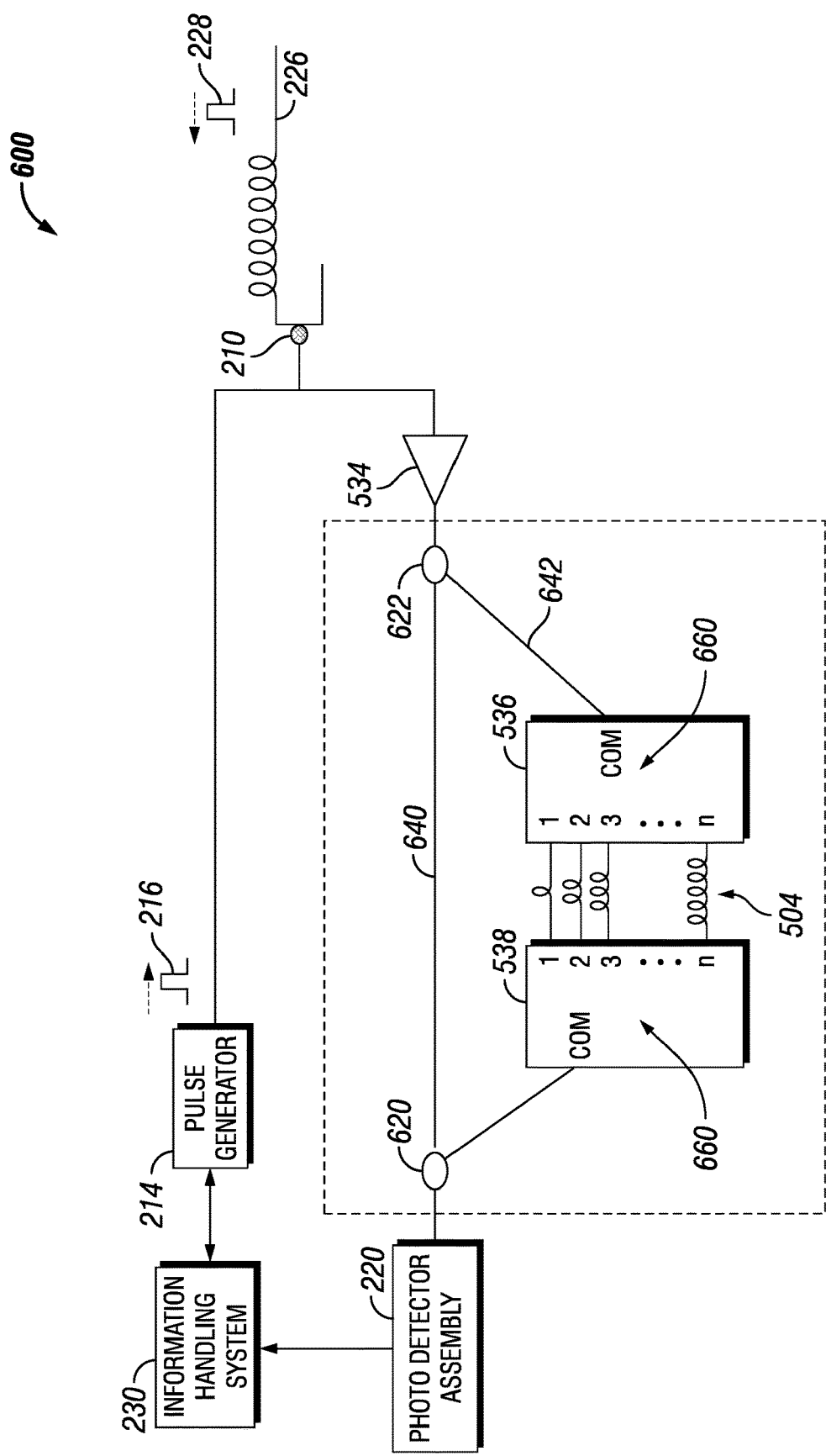
FIG. 6 depicts a distributed acoustic sensing system in accordance with an alternative embodiment of the present disclosure.

Referring now to FIG. 6, an exemplary system for performing Distributed Acoustic Sensing (DAS) according to an alternative embodiment of the present disclosure is referenced generally by reference numeral 600. As shown in FIG. 6, an interferometer 502 may be disposed between an optical gain device 534 and photo detector assembly 220, although other configurations are possible. The optical gain device 534 may be any suitable amplifier such as an EDFA. As shown in FIG. 6, the optical fiber 226 may be disposed between the interferometer 502 and the pulse generator 214 but other configurations are possible. The optical fiber 226 may be lowered downhole. Specifically, the optical fiber 226 may be coupled to a casing or tubing.

As shown in FIG. 6, the interferometer 502 may include a first coupler 622, a first arm 640, a second arm 642, a first optical switch 536, a second optical switch 538, a plurality of fiber coils 504, and a second coupler 620. The second arm 642 of the interferometer 502 may be coupled to the first optical switch 536. The first optical switch 536 may be coupled to the second optical switch 538 via the plurality of fiber coils 504. Each optical switch 536 and 538 includes a number of ports 660 that may be selectively engaged to direct light through the associated fiber coils 504.

In operation of the system 600, the pulse generator 214 may generate a first optical pulse 216 which is transmitted through an optical fiber to the first coupler 210. The first coupler 210 may direct the first optical pulse 216 through the optical fiber 226. At least a portion of the optical fiber 226 may be arranged in coils 218. As the pulse 216 travels through the optical fiber 226, imperfections in the optical fiber 226 may cause light to be reflected back along the optical fiber 226. Backscattered light 228 according to Rayleigh scattering may be returned from every point along the optical fiber 226 along the length of the optical fiber 226. This backscatter effect may be referred to as Rayleigh backscatter. The optical fiber 226 may be terminated with a low reflection device (not shown). In certain implementations, the low reflection device (not shown) may be a fiber coiled and tightly bent to violate Snell's law of total internal reflection such that all the remaining energy is sent out of the fiber. In other implementations, the low reflection device (not shown) may be an angle cleaved fiber. In still other implementations, the low reflection device (not shown) may be a coreless optical fiber with high optical attenuation. In still other implementations, the low reflection device (not shown) may be a termination, such as the AFL Endlight.

Still referring to FIG. 6, the backscattered light 228 may travel back through the optical fiber 226 until it reaches the optical gain device 534. The light may then travel to a second coupler 622. The second coupler may split the optical pulse between a first arm 640 and a second arm 642. The light that is transmitted via the first arm 640 will travel with no delays from the second coupler 622 to the third coupler 620. The light that is sent to the second arm 642 will travel with a controlled delay through the first switch 536 and one fiber coil 504. The light will travel into a selected fiber coil 504 according to an active port 660 in the first optical switch 536. The first optical switch 536 and the second optical switch 538 are preferably 1×n switches such that only one port of each optical switch may be active at any given time. For example, light may travel from port 1 of the first switch 536 to port 1 of the second switch 538. Alternatively, light may travel from port n of the first switch 536 to port n of the second switch 538. The state (active or not active) of the ports 660 may be controlled by an information handling system 230. The portion of the light that traveled through the first arm 640 is then recombined with the light that traveled through the second arm 642 and first and second optical switches 536 and 538 at a third coupler 620. The two portions of light may be separated in time by a delay proportional to the difference in path length between the length of the second arm 642 (including traveling through the second arm 642, the first optical switch 536, the selected fiber coil 504, the second optical switch 538, and to the third coupler 620) and the path length of the first arm 640. Use of the optical switches 536 and 538 eliminates the need to use any optical gain elements within the interferometer 502 because the first and second optical switches 536 and 538 may be used to select a particular singular path delay. This is implicitly efficient as all of the light that travels through the second arm 642 passes through that same delay.

Still referring to FIG. 6, the use of the first and second optical switches 536 and 538 allows for optical efficiencies because only one port of each set of ports 660 may be selectively activated in each optical switch 536 and 538 at any given time. Thus, the light may travel through only one selected fiber coil 504. As compared to other embodiments, such as those described in connection with FIGS. 3 and 4, the embodiment shown in FIG. 6 is more optically efficient and therefore preserves optimum sensitivity of the system 600. For example, it is not necessary to use an optical gain device on each fiber coil 504 or anywhere within the interferometer 502 because the first switch 536 may control which single fiber coil 504 receives light. Activation of a port 560 within each of the optical switches 536 and 538 therefore controls the length of the path delay. This is an efficient arrangement because all of the light that travels through the second arm 642 passes through the same selected fiber coil 504 and therefore the same path delay. The first and second optical switches 536 and 538 are passive during operation of the system 600 and do not add any excess noise during operation.

Still referring to FIG. 6, as discussed with respect to FIG. 3, the backscattered interfered light may be representative of a downhole condition. The downhole condition may include, for example, perforating, operating downhole hardware, monitoring downhole pumps, sensing acoustic signals during fracturing and in-flow stimulation, water injection, production monitoring, flow regimes, reflection seismic, microseismic, and acoustic events related to well-bore integrity (e.g., leaks, cross-flow, and formation compaction). The interferometric signal may also be representative of a condition on pipelines, flow-lines and risers related to flow, leaks, integrity, pigging and maintenance. The interferometric signal may also be representative of conditions on subsea equipment where rotating equipment cause vibration and/or acoustic noise. Similarly, the interferometric system signal may be representative of a condition on infrastructure and security monitoring where it may be beneficial to dynamically vary the optical path length in the system 600. The spatial resolution and sensitivity of the system 600 may be tuned by changing which fiber coil 504 is active by activating a different port 660. As discussed with respect to FIG. 3, the pulse generator 214 may be operable to vary the optical pulse width. Further, the differential path length difference between the first arm 640 and the second arm 642 (including traveling through the second arm 642, the first optical switch 536, a selected fiber coil 504, the second optical switch 538, and to the third coupler 620) may be varied. In this way, the spatial resolution of the system 600 may be varied.

Figure 7:
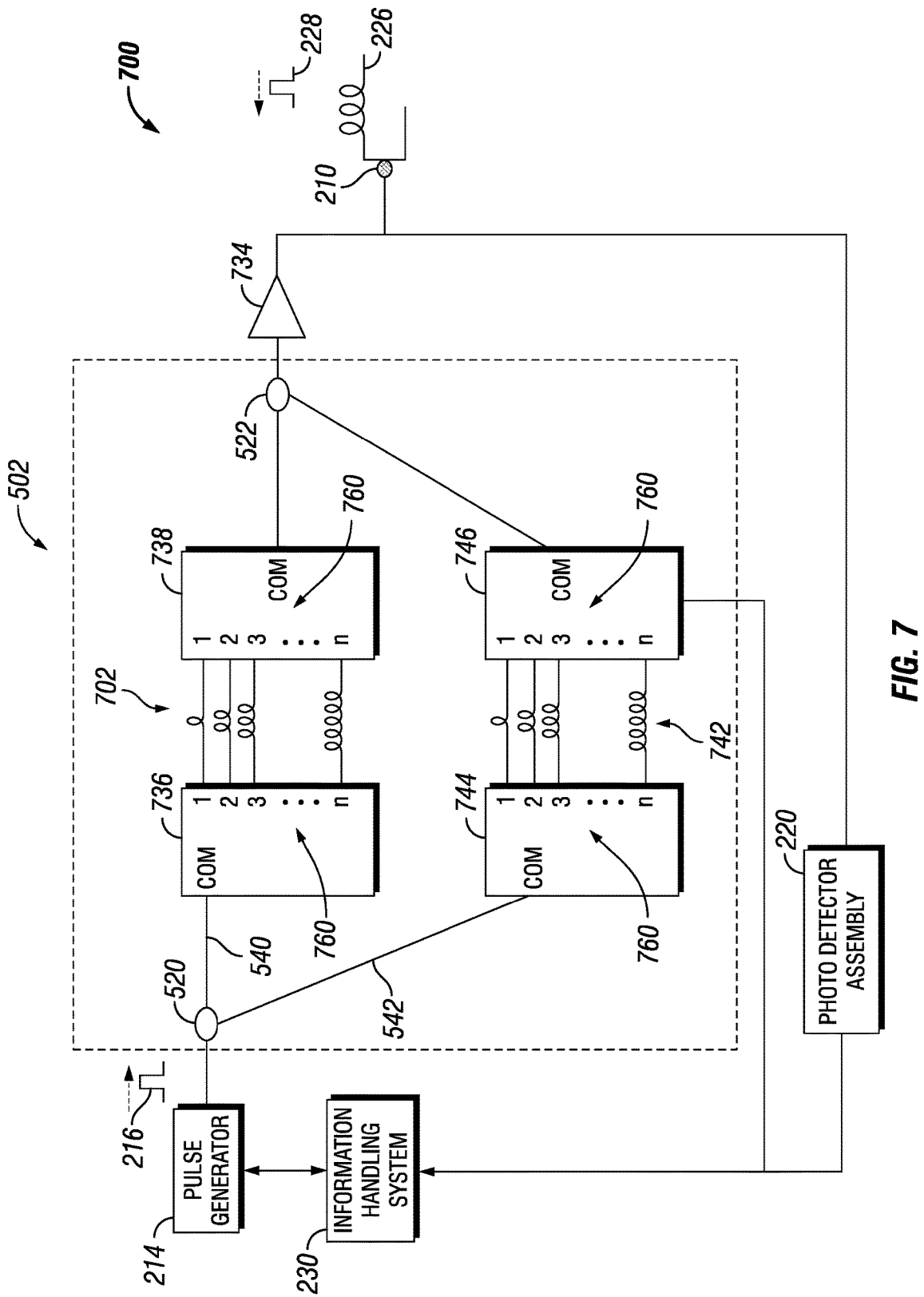
FIG. 7 depicts a distributed acoustic sensing system in accordance with an alternative embodiment of the present disclosure.

Referring now to FIG. 7, an exemplary system for performing Distributed Acoustic Sensing (DAS) according to an alternative embodiment of the present disclosure is referenced generally by reference numeral 700. As shown in FIG. 7, an interferometer 502 may be disposed between a pulse generator 214 and an optical gain device 734, although other configurations are possible. The optical gain device 734 may be any suitable amplifier such as an EDFA. The interferometer 502 may optionally be a pulse delay diplexer. The optical fiber 226 may be lowered downhole. Specifically, the optical fiber 226 may be coupled to a casing or tubing.

As shown in FIG. 7, the interferometer 502 may include a first coupler 520, a first arm 540, a second arm 542, a first optical switch 736, a second optical switch 738, a third optical switch 744, a fourth optical switch 746, and a second coupler 522. The first and second optical switches 736 and 738 may be coupled by a first plurality of fiber coils 702. The third and fourth optical switches 744 and 746 may be coupled by a second plurality of fiber coils 742. Each fiber coil within the first plurality of fiber coils 702 and the second plurality of fiber coils 742 may have a different length. The first arm 540 may be coupled to the first optical switch 736. The second arm 542 may be coupled to the third optical switch 744. Each optical switch includes a number of ports 760 that may be selectively engaged to direct light through the associated fiber coils 702 or 742.

In operation of the system 700, the pulse generator 214 may generate a single pulse that may be split in the first coupler 520 between a first arm 540 and a second arm 542. A first portion of light that is transmitted via the first arm 540 will travel to the first optical switch 736 and with a controlled delay through a selected fiber coil 702. A second portion of light that is sent to the optical fiber 542 will travel to the third optical switch 744 and with a controlled delay through a selected fiber coil 742. The first and second portions of light will each travel into a selected path according to an active port 760 in the first optical switch 736 and third optical switch 744. The state (active or not active) of the ports 760 may be controlled by an information handling system 230. The first optical switch 736, the second optical switch 738, the third optical switch 744, and the fourth optical switch 746 are preferably 1×n switches such that only one port of each optical switch may be active at any given time. For example, light may travel from port 1 of the first optical switch 736 to port 1 of the second optical switch 738. Alternatively, light may travel from port n of the first switch 736 to port n of the second optical switch 738. The portion of the light that traveled through the first arm 540 is then recombined with the light that traveled through the second arm 542 at the second coupler 522. The two portions may be separated in time by a delay proportional to the difference in path length between the selected fiber coil of the first plurality of fiber coils 702 and the selected fiber coil of the second plurality of fiber coils 742. Use of the optical switches 736, 738, 744, and 746 eliminates the need to use any optical gain elements in the interferometer 502 because the first and second optical switches 736 and 738 may be used to select a singular path delay for the top arm of the interferometer 502, and the third and fourth optical switches 744 and 746 may be used to select a singular path delay for the bottom arm of the interferometer 502. After the two portions of the optical pulse are combined at the second coupler 522, each portion of the pulse may be amplified using an optical gain device 734. Both portions may generate backscattered light as they travel down the optical fiber 226. The backscattered light from the first portion may then interfere with the backscattered light from the second portion. The two portions of backscattered light may interfere in the optical fiber 226, and they may travel in the optical fiber 226 to the photodetector assembly 220, where the backscattered interfered light may be converted to an electrical signal.

Still referring to FIG. 7, the use of the optical switches 736, 738, 744, and 746 allows for optical efficiencies because only one port of the ports 760 may be selectively turned on in each of the first optical switch 736 and the third optical switch 744. Thus, the light may travel through only one of the first plurality of fiber coils 702 and one of the second plurality of fiber coils 742. As compared to other embodiments, such as those described in connection with FIGS. 3 and 4, the embodiment shown in FIG. 7 is more optically efficient and therefore preserves optimum sensitivity of the system 700. For example, it is not necessary to use an optical gain device on each fiber coil 702 and 742 or anywhere within the interferometer 502. Excess optical gain devices may add noise to the optical signal. Instead, the first optical switch 736 and third optical switch 744 may control which singular fiber coil 702 and which singular fiber coil 742 receive light, thereby controlling the lengths of the path delays. This is an efficient arrangement because all of the light that travels through the first arm 540 passes through the same fiber coil 702 and therefore the same path delay. Likewise, all of the light that passes through the second arm 542 travels through the same selected fiber coil 742 and therefore the same path delay. The optical switches 736, 738, 744, and 746 are passive during operation of the system 700 and do not add any excess noise during operation.

Still referring to FIG. 7, as discussed with respect to FIG. 3, the backscattered interfered light may be representative of a downhole condition. The downhole condition may include, for example, perforating, operating downhole hardware, monitoring downhole pumps, sensing acoustic signals during fracturing and in-flow stimulation, water injection, production monitoring, flow regimes, reflection seismic, microseismic, and acoustic events related to well-bore integrity (e.g., leaks, cross-flow, and formation compaction). The interferometric signal may also be representative of a condition on pipelines, flow-lines and risers related to flow, leaks, integrity, pigging and maintenance. The interferometric signal may also be representative of conditions on subsea equipment where rotating equipment cause vibration and/or acoustic noise. Similarly, the interferometric system signal may be representative of a condition on infrastructure and security monitoring where it may be beneficial to dynamically vary the optical path length in the system 700. The spatial resolution and sensitivity of the system 700 may be tuned by changing which of the ports 760 (and therefore which of the corresponding fiber coils 702 and 742) are active. Thus, the differential path length difference between the first arm 540 of the interferometer 502 and the second arm 542 of the interferometer 502 may be varied. As discussed with respect to FIG. 3, the pulse generator 214 may be operable to vary the optical pulse width. In this way, the spatial resolution of the system 700 may be varied.

Figure 8:
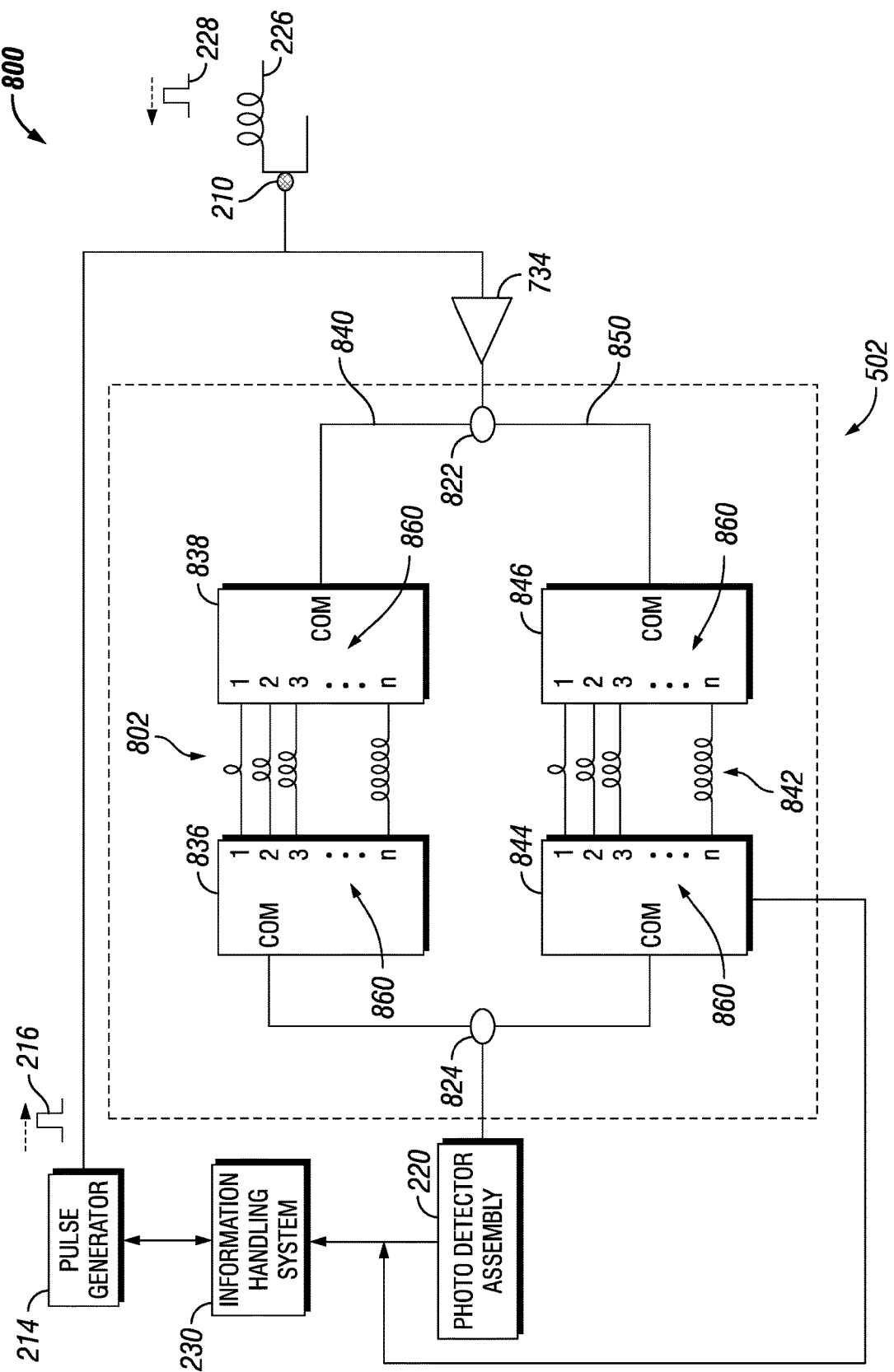
FIG. 8 depicts a distributed acoustic sensing system in accordance with an alternative embodiment of the present disclosure.

Referring now to FIG. 8, an exemplary system for performing Distributed Acoustic Sensing (DAS) according to an alternative embodiment of the present disclosure is referenced generally by reference numeral 800. As shown in FIG. 8, an interferometer 502 may be disposed between an optical gain device 734 and a photo detector assembly 220, although other configurations are possible. The optical gain device 734 may be any suitable amplifier such as an EDFA. As shown in FIG. 8, the optical fiber 226 may be disposed between the interferometer 502 and the pulse generator 214 but other configurations are possible. The optical fiber 226 may be lowered downhole. Specifically, the optical fiber 226 may be coupled to a casing or tubing.

As shown in FIG. 8, the interferometer 502 may include a second coupler 822, a first arm 840, a second arm 850, a first optical switch 838, a second optical switch 836, a first plurality of fiber coils 802, a third optical switch 846, a fourth optical switch 844, a second plurality of fiber coils 842, and a third coupler 824. The first optical switch 838 may be coupled to the second optical switch 836 via the first plurality of fiber coils 802. The third optical switch 846 may be coupled to the fourth optical switch 844 via the second plurality of fiber coils 842. Each fiber coil within the first plurality of fiber coils 802 and the second plurality of fiber coils 842 may have a different length. The first arm 840 may be coupled to the first optical switch 838. The second arm 850 may be coupled to the third optical switch 846. Each optical switch 838, 836, 846, and 844 includes a number of ports 860 that may be selectively engaged to direct light through the associated fiber coils 802 and 842.

In operation of the system 800, the pulse generator 214 may generate a first optical pulse 216 which is transmitted through an optical fiber to the first coupler 210. The first coupler 210 may direct the first optical pulse 216 through the optical fiber 226. At least a portion of the optical fiber 226 may be arranged in coils 218. As the pulse 216 travels through the optical fiber 226, imperfections in the optical fiber 226 may cause light to be reflected back along the optical fiber 226. Backscattered light 228 according to Rayleigh scattering may be returned from every point along the optical fiber 226 along the length of the optical fiber 226. This backscatter effect may be referred to as Rayleigh backscatter. The optical fiber 226 may be terminated with a low reflection device (not shown). In certain implementations, the low reflection device (not shown) may be a fiber coiled and tightly bent to violate Snell's law of total internal reflection such that all the remaining energy is sent out of the fiber. In other implementations, the low reflection device (not shown) may be an angle cleaved fiber. In still other implementations, the low reflection device (not shown) may be a coreless optical fiber with high optical attenuation. In still other implementations, the low reflection device (not shown) may be a termination, such as the AFL Endlight.

Still referring to FIG. 8, the backscattered light 228 may travel back through the optical fiber 226 until it reaches the optical gain device 734. The light may then travel to a second coupler 822. The second coupler 822 may split the optical pulse between a first portion that may travel through a first arm 840 of the interferometer 502 and a second portion that may travel through a second arm 850 of the interferometer 502. The first portion of the pulse, which is transmitted via the first arm 840, will travel to the first optical switch 838 and with a controlled delay through a selected fiber coil in the first plurality of fiber coils 802. The second portion of the pulse, which is sent to the second arm 850, will travel to the third optical switch 846 and with a controlled delay through a selected fiber coil in the second plurality of fiber coils 842. In each of the interferometer arms 840 and 850, the light will travel into a selected path according to the active port in each of the optical switches. The first optical switch 838, the second optical switch 836, the third optical switch 846, and the fourth optical switch 844 are preferably 1×n switches such that only one port on each optical switch may be active at any given time. For example, light may travel from port 1 of the first switch 838 to port 1 of the second switch 836. Alternatively, light may travel from port n of the first switch 838 to port n of at the second optical switch 836. The first portion of the pulse, which traveled through the first arm 840, is then recombined with the second portion of the pulse, which traveled through the second arm 850, at a third coupler 824. The two portions of the pulse may be separated in time by a delay proportional to the difference in path length between the length of the first arm 840 (including traveling through the first arm 840, the first optical switch 838, the selected fiber coil 802, the second optical switch 836, and to the third coupler 620) and the path length of the second arm 850 (including traveling through the second arm 850, the third optical switch 846, the selected fiber coil 842, the fourth optical switch 844, and to the third coupler 824). Use of the optical switches 836, 838, 844, and 846 eliminates the need to use any optical gain elements within the interferometer 502 because the first and second optical switches 838 and 836 may be used to select a particular singular path delay. Likewise, the third and fourth optical switches 846 and 844 may be used to select a particular single path delay. This is implicitly efficient as all of the light that travels through the first arm 840 passes through the same delay. Likewise, all of the light that travels through the second arm 850 passes through the same delay. After the two portions of the optical pulse are combined at the third coupler 824, each portion of the pulse may travel to the photo detector assembly 220.

Still referring to FIG. 8, the use of the optical switches 836, 838, 844, and 846 allows for optical efficiencies because only one port of each set of ports 860 may be selectively activated in each optical switch 836, 838, 844, and 846 at any given point in time. Thus, the light may travel through only one selected fiber coil of the first plurality of fiber coils 802 and one selected fiber coil of the second plurality of fiber coils 842. As compared to other embodiments, such as those described in connection with FIGS. 3 and 4, the embodiment shown in FIG. 8 is more optically efficient and therefore preserves optimum sensitivity of the system 800. For example, it is not necessary to use an optical gain device on each fiber coil 802 and 842 or anywhere within the interferometer 502 because the optical switches 838, 836, 846, and 844 control which fiber coils 802 and 842 receive light. Activation of a port 860 within each of the optical switches 838, 836, 846, and 844 therefore controls the lengths of the path delays. This is an efficient arrangement because all of the light that travels through the first arm 840 passes through the same selected fiber coil 802 and therefore the same path delay. Likewise, all of the light that travels through the second arm 850 passes through the same selected fiber coil 842 and therefore the same path delay. The optical switches 838, 836, 846, and 844 are passive during operation of the system 800 and do not add any excess noise during operation.

Still referring to FIG. 8, as discussed with respect to FIG. 3, the backscattered interfered light may be representative of a downhole condition. The downhole condition may include, for example, perforating, operating downhole hardware, monitoring downhole pumps, sensing acoustic signals during fracturing and in-flow stimulation, water injection, production monitoring, flow regimes, reflection seismic, microseismic, and acoustic events related to well-bore integrity (e.g., leaks, cross-flow, and formation compaction). The interferometric signal may also be representative of a condition on pipelines, flow-lines and risers related to flow, leaks, integrity, pigging and maintenance. The interferometric signal may also be representative of conditions on subsea equipment where rotating equipment cause vibration and/or acoustic noise. Similarly, the interferometric system signal may be representative of a condition on infrastructure and security monitoring where it may be beneficial to dynamically vary the optical path length in the system 800. The spatial resolution and sensitivity of the system 800 may be tuned by changing which ports 860, and therefore which of the fiber coils 802 and 842, are active. As discussed with respect to FIG. 3, the pulse generator 214 may be operable to vary the optical pulse width. Further, the differential path length difference between the selected fiber coils 802 and 842 may be varied. In this way, the spatial resolution of the system 800 may be varied.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. Also, the terms in the claims have their plain, ordinary meaning unless otherwise explicitly and clearly defined by the patentee.

What is claimed is:

1. A distributed acoustic sensing system based on coherent Rayleigh scattering, comprising:
   a pulse generator, which generates an optical pulse;
   an interferometer, further comprising:
      a first arm, wherein a first portion of the optical pulse travels through the first arm;
      a second arm, wherein a second portion of the optical pulse travels through the second arm;
      a first optical switch coupled to the second arm and to a first plurality of fiber coils; and
      a second optical switch coupled to the first plurality of fiber coils;
   wherein the first optical switch and the second optical switch each comprise a plurality of ports;
   a photodetector assembly coupled to the interferometer, wherein the photodetector assembly detects backscattered interfered light; and
   an information handling system, which activates one port on the first optical switch and one port on the second optical switch so as to delay the optical path length of the second portion of the optical pulse, thereby changing the spatial resolution of the system.

2. The system of claim 1, further comprising:
   a third optical switch coupled to the first arm of the interferometer and coupled to a second plurality of fiber coils; and
   a fourth optical switch coupled to the second plurality of fiber coils,
   wherein the third optical switch and the fourth optical switch each comprise a plurality of ports; and
   wherein the information handling system activates one port on the third optical switch and one port on the fourth optical switch so as to delay the optical path length of the first portion of the optical pulse, thereby changing the spatial resolution of the system.

3. The system of claim 2, wherein the first plurality of fiber coils each has a different length, and wherein the second plurality of fiber coils each has a different length.

4. The system of claim 2, wherein the interferometer is disposed between the pulse generator and an optical fiber.

5. The system of claim 4, wherein the optical fiber is arranged in coils.

6. The system of claim 4, wherein the optical fiber is adapted to be disposed downhole.

7. The system of claim 6, wherein the optical fiber is coupled to at least one of a casing and a tubing.

8. The system of claim 6, wherein the backscattered interfered light is representative of a downhole condition.

9. The system of claim 8, wherein the downhole condition is selected from a group consisting of: perforations, monitoring downhole pumps and hardware, sensing acoustic signals during fracturing and in-flow stimulation, water injection, production monitoring, flow regimes, reflection seismic, micro-seismic, leaks, cross-flow, and formation compaction.

10. The system of claim 4, further comprising:
    a low reflection device coupled to the optical fiber.

11. The system of claim 4, wherein the pulse generator is operable to generate optical pulses having variable pulse widths.

12. The system of claim 11, wherein a portion of an optical pulse is reflected along the optical fiber according to Rayleigh backscatter.

13. The system of claim 2, wherein an optical fiber is disposed between the interferometer and the pulse generator.

14. A method for distributed acoustic sensing comprising:
    sending a first optical pulse down an optical fiber, wherein light from the first optical pulse is backscattered from positions along the length of the optical fiber according to coherent Rayleigh scattering;
    splitting backscattered light from the first optical pulse into a first portion and a second portion;
    activating a first port of a first optical switch, a first port of a second optical switch, a first port of a third optical switch, and a first port of a fourth optical switch;
    sending the first portion into a first arm of an interferometer, wherein the first arm of the interferometer is coupled to a first port of the first optical switch;
    sending the second portion into a second arm of the interferometer, wherein the second arm of the interferometer is coupled to a first port of the third optical switch;
    combining the first and second portions to form an interferometric signal;
    receiving the interferometric signal at a photodetector assembly;
    providing output relating to the interferometric signal to an information handling system.

15. The method of claim 14, further comprising:
    sending a second optical pulse down the optical fiber; and
    varying the activation of a plurality of ports of the first optical switch, the second optical switch, the third optical switch, and the fourth optical switch.

16. A method for distributed acoustic sensing comprising:
    generating a first optical pulse;
    splitting the first optical pulse into a first portion and a second portion;
    activating a first port of a first optical switch, a first port of a second optical switch, a first port of a third optical switch, and a first port of a fourth optical switch;
    sending the first portion into a first arm of an interferometer, wherein the first arm of the interferometer is coupled to the first port of the first optical switch;
    sending the second portion into a second arm of the interferometer, wherein the second arm of the interferometer is coupled to the first port of the third optical switch;
    combining the first portion from the first arm and the second portion from the second arm;
    sending the first and second portions down an optical fiber, wherein light from the first and second portions is backscattered from positions along the length of the optical fiber according to coherent Rayleigh scattering to form an interferometric signal;
    receiving the interferometric signal at a photodetector assembly;
    providing output relating to the interferometric signal to an information handling system.

17. The method of claim 16, further comprising:
generating a second optical pulse; and
varying the activation of a plurality of ports of the first optical switch, the second optical switch, the third optical switch, and the fourth optical switch.

* * * * *